United States Patent
Stamler et al.

(10) Patent No.: US 8,815,297 B2
(45) Date of Patent: Aug. 26, 2014

(54) MODULATION OF BETA 2 ADRENERGIC RECEPTORS BY INHIBITORS OF EGLN3 OR PVHL

(75) Inventors: Jonathan S. Stamler, Chapel Hill, NC (US); Liang Xie, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/256,954

(22) PCT Filed: Mar. 31, 2010

(86) PCT No.: PCT/US2010/000956
§ 371 (c)(1),
(2), (4) Date: Jan. 26, 2012

(87) PCT Pub. No.: WO2010/117423
PCT Pub. Date: Oct. 14, 2010

(65) Prior Publication Data
US 2012/0121720 A1     May 17, 2012

Related U.S. Application Data

(60) Provisional application No. 61/202,733, filed on Mar. 31, 2009.

(51) Int. Cl.
*A61K 35/14*     (2006.01)

(52) U.S. Cl.
USPC .................................................. 424/529

(58) Field of Classification Search
USPC .................................................. 424/529
See application file for complete search history.

(56) References Cited

FOREIGN PATENT DOCUMENTS

WO     2007/009044 A2     1/2007

OTHER PUBLICATIONS

Guo Y. Regulation of the proapoptotic protein BIMEL through its interactions with the tumor suppressor pVHL and the HIF prolyl hydroxylase EGLN3. Interdepartmental Graduate Program in Neuroscience School of Medicine and Dentistry. University of Rochester. 2008.*
Asikainen et al. Improved lung growth and function through hypoxia-inducible factor in primate chronic lung disease of prematurity. FASEB J. 2006;20(10):1698-700.*
Johnson M. The beta-adrenoceptor. Am J Respir Crit Care Med. 1998;158:S146-S153.*
Koditz et al. Oxygen-dependent ATF-4 stability is mediated by the PHD3 oxygen sensor. Blood. 2007;110(10):3610-7.*
Werz et al. Development of 5-lipoxygenase inhibitors—lessons from cellular enzyme regulation. Biochem Pharmacol. 2005;70(3):327-33.*
Pescador et al. Identification of a functional hypoxia-responsive element that regulates the expression of the egl nine homologue 3 (egln3/phd3) gene. Biochem. J. 2005;390:189-197.*
Guo et al., "The von Hippel-Lindau protein sensitizes renal carcinoma cells to apoptotic stimuli through stabilization of BIM(EL)", Oncogene, 2009, vol. 28, No. 16, pp. 1864-1874.
Shenoy et al., "Nedd4 Mediates Agonist-dependent Ubiquitination, Lysosomal Targeting, and Degradation of the beta2-Adrenergic Receptor", Journal of Biological Chemistry, Aug. 8, 2008, vol. 283, No. 32, pp. 22166-22176.
Xie et al., "Oxygen-Regulated beta2-Adrenergic Receptor Hydroxylation by EGLN3 and Ubiquitylation by pVHL", Sci Signal, Jul. 7, 2009, vol. 2, No. 78, pp. 1-21.
International Search Report of International Application No. PCT/US2010/000956, dated Jun. 24, 2010.

* cited by examiner

*Primary Examiner* — Ruth Davis
*Assistant Examiner* — Lynn Y Fan
(74) *Attorney, Agent, or Firm* — Bacon & Thomas, PLLC

(57) ABSTRACT

This present invention relates to methods, compositions, and kits useful for treating a patient having or at risk for developing a disorder associated with decreased expression of β2 adrenergic receptors or need for increased β2 adrenergic receptor activity.

3 Claims, No Drawings ns, and kits useful for treating a patient having or at risk for developing a disorder associated with decreased expression of $\beta_2$ adrenergic receptors or need for increased $\beta_2$ adrenergic receptor activity.

MODULATION OF BETA 2 ADRENERGIC RECEPTORS BY INHIBITORS OF EGLN3 OR PVHL

TECHNICAL FIELD

This invention is directed to methods, compositions, and kits useful for treating a patient having or at risk for developing a disorder associated with decreased expression of $\beta_2$ adrenergic receptors or need for increased $\beta_2$ adrenergic receptor activity.

BACKGROUND OF THE INVENTION

Adrenergic receptors are a family of cell membrane receptors that receive neuronal impulses from postganglionic adrenergic fibers from the sympathetic nervous system. There are at least nine sub-types of adrenergic receptors of which at least three sub-types are beta-adrenergic receptors (βARs) (H. G. Dohlman et al., Annu. Rev. Biochem. 60:653-688 (1991); S. B. Liggett et al., In: Catecholamines, Bouloux, ed. W. B. Sounders, London (1993)). BARs are prototypic G-protein coupled receptors (GPCRs) that play an important role in the regulation of cardiovascular and pulmonary function. β2ARs constitute about 25-30% of the total βARs in the human heart, and are the predominant subtype expressed in both vascular and airway smooth muscle. β2ARs are directly associated with a receptor-channel complex containing G proteins, which activates adenylyl cyclase, cAMP-dependent kinase and the counterbalancing phosphatase, PP2A. The assembly of the signaling complex provides a mechanism that ensures specific and rapid signaling by this G protein-coupled receptor.

Accordingly, β2ARs are expressed in many organs in the body and modulate a variety of physiological functions of the body (J. R. Carstairs et al., Am. Rev. Respir. Dis. 132:541-547 (1985); Q. A. Hamid et al., and Eur. J. Pharmacol. 206:133-138 (1991)). Overexpression of the β2AR greatly increases cardiac contractility and provides a cardioprotective effect (S. B. Liggett et al., Circulation 101, 1707 (2000)). Continuous agonist stimulation induces β2AR ubiquitylation, internalization and degradation (S. K. Shenoy, P. H. McDonald, T. A. Kahout, R. J. Leftkowitz, Science 294, 1307 (2001)), thereby down-regulating the total number of receptors. βAR down-regulation (and dysfunction) is associated with diseases such as heart failure and asthma (H. A. Rodman, W. J. Koch, R. J. Leftkowitz 425, 206 (2002); M. Johnson An J Respir. Crit. Care Med. 158, S146 (1998)).

Given the importance of β2ARs in modulating physiological functions, there is a need in the art for regulating the expression and activity of β2ARs.

The inventors of the present application have discovered that the Von Hippel-Lindau tumor suppressor protein (pVHL)-E3 ligase complex, characterized previously by its regulation of hypoxic inducible factor (HIF) proteins, interacts with and ubiquitylates β2AR, promoting receptor down-regulation. Under normoxic conditions HIF proteins are very unstable due to hydroxylation by a family of proline hydroxylases termed EGL-nine homologs (EGLN).

The interaction of pVHL with the β2AR is dependent on proline hydroxylation, and the dioxygenase EGLN3 interacts directly with the β2AR to serve as an endogenous β2AR prolyl hydroxylase. Following hydroxylation of the β2AR, the pVHL-E3 ligase complex is recruited to and ubiquitylates the β2AR, promoting its down-regulation via proteosomal degradation.

The inventors of the present application have further discovered that the interaction between EGLN3 and β2AR can be manipulated to regulate the expression and activity of β2ARs.

SUMMARY OF THE INVENTION

The present invention is directed to methods, compositions, and kits useful for treating a patient having or at risk for developing a disorder associated with decreased expression of β2ARs or increased β2AR receptor activity.

In a first embodiment, the invention is directed to a method for treating a patient having or at risk for developing a disorder associated with decreased expression of β2ARs or need for increased β2AR activity, comprising administering to said patient a therapeutically effective amount of an inhibitor of EGLN3 or an inhibitor of pVHL.

In one aspect, these disorders include but are not limited to a disorder treated with a beta agonist compound, cardiac contractility dysfunction resulting from decreased expression of β2ARs, asthma, chronic obstructive pulmonary disease (COPD), pulmonary edema, peripheral vascular disease pulmonary edema resulting from reduced expression of β2ARs, a disorder treated with a beta blocker compound, hypertension, nitric oxide donor desensitization of β2ARs, impaired secretion clearance of airways, cystic fibrosis, sickle cell disease, a disorder associated with an impaired sense of smell, Acute Respiratory Distress Syndrome (ARDS), and impaired skeletal muscle function (e.g., dystrophies, neuromuscular diseases, cachexia, weakness, growth and repair of muscle).

In a second embodiment, the invention is directed to a composition comprising i) a therapeutically effective amount of first active ingredient comprising an inhibitor of EGLN3 or an inhibitor of pVHL, and ii) a therapeutically effective amount of a second active ingredient. In one aspect, the second active ingredient is selected for example from the group consisting of NO donor compounds, beta agonists, and beta antagonists.

A third embodiment of the invention is a kit comprising i) a first active ingredient comprising a therapeutically effective amount of an inhibitor of EGLN3 or an inhibitor of pVHL, and ii) a therapeutically effective amount of a second active ingredient. The second active ingredient is selected for example from the group consisting of NO donor compounds, beta agonists, and beta blockers.

The term "therapeutically effective amount" as used herein means an amount sufficient to effect treatment when administered to a patient in need of treatment.

The term "treatment" as used herein refers to therapy of a disease or medical condition in a patient, such as a mammal (particularly a human), and includes: a) ameliorating or inhibiting the disease or medical condition; b) suppressing the disease or medical condition, i.e., slowing or arresting the development of the disease or medical condition in a patient; or c) alleviating the symptoms of the disease or medical condition in a patient.

The phrase "a disorder associated with decreased expression of β2ARs or need for increased β2AR activity" includes all disease states and/or conditions that are acknowledged now, or that are found in the future, to be associated with decreased expression of β2AR or need for increased β2AR activity.

The terms "inhibitor of EGLN3 enzyme activity", "inhibitor of EGLN3" and "EGLN3 inhibitor" are used interchangeably and are used herein to mean any agent that reduces activity of the EGLN3 enzyme.

DETAILED DESCRIPTION OF THE INVENTION

As noted above, a first aspect of the invention is directed to a method for treating a patient having or at risk for developing a disorder associated with decreased expression of β2AR or need for increased β2AR activity, comprising administering to said patient a therapeutically effective amount of an inhibitor of EGLN3 or an inhibitor of pVHL.

In one aspect of this embodiment, the inhibitor of EGLN3 is a succinate dehydrogenase compound, a 2-oxoglutarate analog, an iron chelator, an iron-displacing metal, a peptide inhibitor of EGLN3, antisense to EGLN3, siRNA that interferes with EGLN3 expression, or an aptamer of EGLN3.

The succinate dehydrogenase compound is selected from the group consisting of, but not limited to, malonic acid, 3-nitroproprionic acid, and theonyl trifluoracetone.

The 2-oxoglutarate analog is selected from the group consisting of dimethyloxalylglycine (DMOG), N-oxalylglycine, N-oxalyl-2S-alanine, and N-oxalyl-2R-alanine DMOG is a preferred inhibitor used in the invention.

In addition, SiRNAs that suppress VHL are used as inhibitor (e.g., sense, 5'-GCAAAUACUACGUCAAGGAUU-3' (SEQ ID NO: 1); antisense, 5'-UCCUUGACGUAGUAU-UUGCUU-3' (SEQ ID NO: 2) and sense, 5'-UUCAGGAAU-UUAACUAGGAUU-3' (SEQ ID NO: 3); and antisense, 5'-UCCUAGUUAAAUUCCUGAAUU-3' (SEQ ID NO: 4); Genbank Accession Number, EGLN3 NM_022703).

Peptides derived from EGLN3 such as EGLN3 (EAIS-FLLSLIDRLVLY) (SEQ ID NO: 5) can also be used. The peptide inhibits binding of EGLN3 to the β2AR and thereby increases receptor expression in cells.

Additional compounds that can inhibit EGLN3 are described in WO 2007/009044; WO 2003/049686; WO 2002/074981; WO 2003/080566; and WO 2004/108681, the entirety of each is incorporated herein by reference.

The inhibitors of EGLN3 inhibit EGLN3 enzyme activity, and can optionally inhibit activity of related enzymes (e.g., EGLN1, EGLN2, etc.).

In one aspect, the EGLN3 inhibitor selectively inhibits EGLN3, i.e., shows greater inhibition of EGLN3 than of related enzymes such as EGLN1 and EGLN2.

The inhibitor of EGLN3 enzyme activity is for example the form of a pharmaceutically acceptable salt. The salts are prepared from pharmaceutically acceptable non-toxic bases including inorganic bases and organic bases. Examples of salts derived from inorganic bases include aluminum, ammonium, calcium, copper, ferric, ferrous, lithium, magnesium, manganic salts, manganous, potassium, sodium, zinc, and the like. In a particular aspect, the salt is an ammonium, calcium, magnesium, potassium, or sodium salt.

Pharmaceutically acceptable organic non-toxic bases include salts of primary, secondary, and tertiary amines, benethamine, N,N'-dibenzylethylenediamine, diethylamine, 2-diethylaminoethanol, 2-dimethylaminoethanol, diethanolamine, ethanolamine, ethylenediamine, N-ethylmorpholine, N-ethylpiperidine, epolamine, glucamine, glucosamine, histidine, hydrabamine, isopropylamine, lysine, methylglucamine, meglumine, morpholine, piperazine, piperidine, polyamine resins, procaine, purines, theobromine, triethylamine, tripropylamine, trolamine, and tromethamine. Examples of other salts include arecoline, arginine, barium, betaine, bismuth, chloroprocaine, choline, clemizole, deanol, imidazole, and morpholineethanol. The salt are preferably tris salts.

The EGLN3 inhibitors are administered orally, topically, enterally, parenterally by injection or infusion, by inhalation, or by other forms of administration.

For oral administration, suitable daily dosages are for example between about 5-4000 mg, more preferably 5-1000 mg, and more preferably 10-100 mg administered orally once-daily, twice-daily or three times-daily, continuously (every day) or intermittently (e.g., 3-5 days a week). For example, when used to treat a particular disease, the dose of the inhibitor can range between about 2 mg to about 2000 mg per day, 2 mg to about 1000 mg per day, 2 mg to about 500 mg per day, 2 mg to about 500 mg per day, 2 mg to about 100 mg per day, or 10 mg to about 100 mg per day.

The EGLN3 inhibitor can also be administered by the pulmonary route, including but not limited to intratracheal instillation, intratracheal delivery of liposomes, insufflation and aerosol inhalation. Aerosols can also be used in intranasal applications. Typically, an intravenous formulation is prepared which contains a concentration of the inhibitor of between about 1.0 mg/ml to about 50 mg/ml, preferably 1.0 mg/ml to about 25 mg/ml, and more preferably 1.0 mg/ml to about 10 mg/ml. In one example, a sufficient volume of intravenous formulation is administered to a patient in a day such that the total dose for the day is between about 10 and about 2500 mg/ml, preferably 10 and about 1500 mg/ml, and more preferably 10 and about 500 mg/ml.

The inhibitor can also be administered in intranasal form via topical use of suitable intranasal vehicles, or via transdermal routes, using those forms of transdermal skin patches well known to those of ordinary skill in the art. To be administered in the form of a transdermal delivery system, the dosage administration will be continuous rather than intermittent throughout the dosage regime.

The inhibitor is administered once daily, or divided into multiple daily doses such as twice daily, and three times daily. For administration once a day, a suitably prepared medicament would therefore contain all of the needed daily dose. For administration twice a day, a suitably prepared medicament would therefore contain half of the needed daily dose. For administration three times a day, a suitably prepared medicament would therefore contain one third of the needed daily dose.

In addition, the administration is continuous, i.e., every day, or intermittently. The terms "intermittent" or "intermittently" as used herein means stopping and starting at either regular or irregular intervals. The inhibitors of EGLN3 are used alone or in combination with other compounds. A combination of at least two compounds is formulated and administered separately, or by administering at least two compounds together. The two or more agents are preferably administered within minutes of each other, within 1, 2, 3, 6, 9, 12, 15, 18, or 24 hours of each other, within 1, 2, 3, 4, 5, 6, 7, 8, 9, 10, 12, 14 days of each other, or within 2, 3, 4, 5, 6, 7, 8, 9, or 10 weeks of each other.

A facet of the first embodiment is that the disorders associated with decreased expression of β2ARs or need for increased β2AR activity include, but are not limited to a disorder treated with a beta agonist compound, cardik contractility dysfunction resulting from decreased expression of β2ARs, asthma, COPD, peripheral vascular disease, pulmonary edema including pulmonary edema resulting from reduced expression of β2ARs, a disorder treated with a beta blocker compound, hypertension, nitric oxide donor desensitization of β2ARs, impaired secretion clearance of airways, cystic fibrosis, sickle cell disease, and a disorder associated with an improved sense of smell.

The inhibitor of EGLN3 is administered with an additional active ingredient or therapy used for treating disorders associated with the decreased expression of β2AR or a need for increased β2AR activity. For example, the additional active ingredient is a beta agonist compound, a beta blocker, or an active ingredient used to treat cardiac contractility dysfunction resulting from decreased expression of β2ARs, asthma, COPD, peripheral vascular disease, pulmonary edema resulting from reduced expression of β2ARs, hypertension, nitric oxide donor desensitization of β2ARs, disorders associated with an impaired secretion clearance of airways, cystic fibrosis, sickle cell disease, and a disorder associated with impaired sense of smell.

The additional active ingredient can also be a NO donor compound (e.g., C—N—S or O NO donor compounds). An NO donor compound donates nitric oxide or a related redox species and more generally provides nitric oxide bioactivity that is an activity which is identified with nitric oxide, e.g., vasorelaxation or stimulation or inhibition of a receptor protein. NO donors are described in "Methods in Nitric Oxide Research," edited by Feelisch, M., and Stamler, J. S., John Wiley & Sons, New York, 1996, pages 71-115, the entirety of which is incorporated herein by reference.

Examples of useful compounds are C-nitroso compounds, S-nitroso compounds, sodium nitroprusside, ethyl nitrite, nitroglycerin, SIN1 which is molsidomine, furoxamines, N-hydroxy amines (N-nitrosoamine), perfluorocarbons that have been saturated with NO or a hydrophobic NO donor.

C-nitroso compounds, wherein nitroso is attached to a tertiary carbon can also be used with the invention. The C-nitroso compounds described in U.S. Pat. No. 7,030,238 and "Methods in Nitric Oxide Research," edited by Feelisch, M. and Stamler, J. S., John Wilen & Sons, New York (1996) are incorporated herein by reference (See also Rehse, K, et al., Arch. Pharm. Pharm. Med. Chem. 331, 104-110 (1998), Rehse, K, et al., Arch. Pharm. Pharm. Med. Chem., 331, 79-84 (1998), and Sklyar, Yu. E., et al., Khimiya Geterotsiklicheskikh Soedinenii 5, 70-73 (1969)).

S-nitroso compounds including. S-nitrosothiols (e.g., S-nitrosoglutathione, S-nitroso-N-acetylpenicillamine, S-nitroso-cysteine and ethyl ester thereof S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin) can also be utilized as the additional active ingredient the invention.

In one aspect, the inhibitor of EGLN3 or pVHL and NO donor compounds is administered together, or in combination with an active ingredient and treatments for treating disorders associated with decreased expression of β2ARs or need for increased β2AR activity include (e.g., a disorder treated with a beta agonist compound, cardiac contractility dysfunction resulting from decreased expression of β2ARs, asthma, COPD, peripheral vascular disease, pulmonary edema including pulmonary edema resulting from reduced expression of β2ARs, a disorder treated with a beta blocker compound, hypertension, nitric oxide donor desensitization of β2ARs, impaired secretion clearance of airways, cystic fibrosis, sickle cell disease, and a disorder associated with an improved sense of smell).

In a further aspect, the combination of administering the inhibitor of i) pVHL or EGLN3 and ii) an additional active ingredient allows for the amount of i) inhibitor of pVHL or EGLN3 and/or ii) additional active ingredient to be administered in amounts less than (e.g., 10-75% by weight, preferably 25-50% by weight, and more preferably 30-40% by weight less) those discussed in this application for the inhibitor and as typically prescribed for the additional active ingredients.

It should be apparent to a person skilled in the art that the various modes of administration, dosages and dosing schedules described herein merely set forth specific aspects and should not be construed as limiting the broad scope of the invention. Any permutations, variations and combinations of the dosages and dosing schedules are included within the scope of the present invention.

In a further aspect, the patient has or is at risk of developing a disorder that is treated with a beta agonist compound.

These disorders include for example anaphylactic shock, cardiac arrest, severe hypotension, septic shock, acute heart failure, cardiogenic shock, acute renal failure, refractory heart failure, bradycardia, and atrioventricular blocking. Beta agonists bind to BARs on cardiac and smooth muscle tissues. They also have important actions in other tissues, such as bronchial smooth muscle (relaxation), the liver (stimulate glycogenolysis) and kidneys (stimulated renin release). BARs normally bind to norepinephrine released by sympathetic adrenergic nerves, and to circulating epinephrine.

β-agonists mimic the actions of sympathetic adrenergic stimulation acting through βARs. Overall, the effect of β agonists is cardiac stimulation (increased heart rate, contractility, conduction velocity, relaxation) and systemic vasodilation. Arterial pressure can increase, but not necessarily because the fall in systemic vascular resistance offsets the increase in cardiac output. Therefore, the effect on arterial pressure depends on the relative influence on cardiac versus vascular βARs.

β-agonists can also increase skeletal muscle mass and decrease body fat. In this regard, β-agonists are used to treat disorders involving skeletal muscle function (e.g., dystrophies, neuromuscular diseases, cachexia, weakness, growth and repair of muscle), combat sarcopenia, cancer cachexia, denervation, and neuromuscular diseases, with the aim of attenuating the muscle wasting and associated muscle weakness, and to enhance muscle growth and repair after injury (see Gordon S. Lynch and James G. Ryall Physiol. Rev. 88: 729-767, 2008).

The inhibitors of EGLN3 and pVHL are administered with or without a therapeutically effective amount of a B agonist compound such as epinephrine, norepinephrine, dopamine, dobutamine, ritodrine, formoterol, fenoterol, procaterol, isoproterenol, albuterol, ventolin, proventil, metaproterenol, alupent, pirbuterol, terbutaline, isoetharine, levalbuterol, or salmeterol (Goodman & Gilman's, *The Pharmacological Basis of Therapeutics*, McGraw-Hill Medical Publishing Division, Tenth Edition, pg. 227-232, 2001, incorporated herein by reference).

The inhibitors of EGLN3 and/or pVHL along with the administration of these inhibitors are in accordance with this embodiment as discussed above. Additional active ingredients as discussed in this embodiment can optionally be administered.

In a further aspect, the patient has or is at risk of developing cardiac contractility dysfunction resulting from decreased expression of β2ARs. In particular, the disorder is arrhythmia or cardiogenic shock.

The inhibitors of EGLN3 and pVHL are administered with or without a therapeutically effective amount of β agonist compounds such as epinephrine, norepinephrine, dopamine, dobutamine, ritodrine, formoterol, fenoterol, procaterol, isoproterenol, albuterol, ventolin, proventil, metaproterenol, alupent, pirbuterol, terbutaline, isoetharine, levalbuterol, or salmeterol (See Goodman & Gilman's, *The Pharmacological*

Basis of Therapeutics, McGraw-Hill Medical Publishing Division, Tenth Edition, pg. 227-232, 2001, incorporated herein by reference).

The inhibitors of EGLN3 and/or pVHL along with the administration of these inhibitors are in accordance with this embodiment as discussed above. Additional active ingredients as discussed in this embodiment can optionally be administered.

Asthma

In a further aspect, the patient has or is at risk of developing asthma. Accordingly, the inhibitors are administered alone or in combination with a therapeutically effective amount of anti-asthmatic compounds such as salmeterol, formoterol, bambuterol, albuterol, salbutamol, levalbuterol, terbutaline, bitolterol, and glucocorticoids (e.g., ciclesonide, beclomethasone, budesonide, flunisolide, fluticasone, mometasone, and triamcinolon).

The compounds are preferably administered in the form of an aerosol. (See Goodman & Gilman's, *The Pharmacological Basis of Therapeutics*, McGraw-Hill Medical Publishing Division, Tenth Edition, pg. 735-748, 2001, incorporated herein by reference).

The inhibitors of EGLN3 and/or pVHL along with the administration of these inhibitors are in accordance with this embodiment as discussed above. Additional active ingredients as discussed in this embodiment can optionally be administered.

In a further aspect, the patient has or is at risk of developing chronic obstructive pulmonary disease (COPD).

The inhibitors of EGLN3 and pVHL are administered alone or in combination with a medicine that opens the airways by relaxing the muscles around the airways that can tighten during a COPD event. β-agonists as discussed above are administered orally or by inhalers. Activation of the β2ARs relaxes the muscles surrounding the airways and opens the airway. Dilating airways helps to relieve the symptoms such as dyspnea (See Goodman & Gilman's, *The Pharmacological Basis of Therapeutics*, McGraw-Hill Medical Publishing Division, Tenth Edition, pg. 749-750, 2001, incorporated herein by reference).

The inhibitors of EGLN3 and/or pVHL along with the administration of these inhibitors are in accordance with this embodiment as discussed above. Additional active ingredients as discussed in this embodiment can optionally be administered.

In a further aspect, the patient has or is at risk of developing pulmonary edema. Pulmonary edema is fluid accumulation in the lungs. It leads to impaired gas exchange and may cause respiratory failure. It is due to either failure of the heart to remove fluid from the lung circulation ("cardiogenic pulmonary edema") or a direct injury to the lung parenchyma ("non-cardiogenic pulmonary edema"). Treatment depends on the cause, but focuses on maximizing respiratory function and removing the cause. Focus is initially on maintaining adequate oxygenation. This may happen with high-flow oxygen, noninvasive ventilation (either continuous positive airway pressure (CPAP) or variable positive airway pressure (VPAP)) or mechanical ventilation in extreme cases.

When circulatory causes have led to pulmonary edema, treatment with beta blockers, intravenous nitrates (glyceryl trinitrate), and loop diuretics, such as furosemide or bumetanide, is the mainstay of therapy. These improve both preload and afterload, and aid in improving cardiac function.

The inhibitors of EGLN3 and/or pVHL along with the administration of these inhibitors are in accordance with this embodiment as discussed above. Additional active ingredients as discussed in this embodiment can optionally be administered.

In another aspect, the patient can have or be at risk of developing pulmonary edema resulting from reduced expression of $\beta_2$ARs.

The inhibitors of EGLN3 and pVHL are administered alone or in combination with a therapeutically effective amount of oxygen for the treatment of pulmonary edema. For example, the patient receives oxygen through a face mask or nasal cannula—a flexible plastic tube with two openings that deliver oxygen to each nostril.

Depending on the severity of the condition, the patient might also receive a therapeutically effective amount of a preload reducer (e.g., furosemide), morphine, afterload reducers (e.g., nitroprusside), aspirin, or blood pressure medications (e.g., angiotensin-converting enzyme (ACE) inhibitors, angiotensin II receptor blockers angiotensin II receptor blockers, beta blockers, calcium channel blockers) in combination with the inhibitor of the invention.

The inhibitors of EGLN3 and/or pVHL along with the administration of these inhibitors are in accordance with this embodiment as discussed above. Additional active ingredients as discussed in this embodiment can optionally be administered.

Peripheral vascular disease (PVD), also known as peripheral artery disease (PAD) or peripheral artery occlusive disease (PAOD), includes diseases caused by the obstruction of large arteries in the arms and legs. PVD can result from atherosclerosis, inflammatory processes leading to stenosis, an embolism or thrombus formation. It causes either acute or chronic ischemia (lack of blood supply), typically of the legs. Most people with PVD are treated with lifestyle changes, medications or both. Medications that are administered optionally in combination with the above-identified inhibitors include beta blockers, cilostazol and pentoxifylline In a preferred feature of this embodiment, inhibitors of EGLN3 and/or pVHL are administered alone or in combination with beta blockers.

In yet another aspect, the inhibitors in accordance with this invention are administered alone or in combination with NO donor compounds.

In yet an even more preferred aspect of this embodiment, the inhibitors are administered alone or in combination with a beta blocker and NO donor compound.

The inhibitors of EGLN3 and/or pVHL and the administration of these inhibitors are in accordance with this embodiment as discussed above. Additional active ingredients as discussed in this embodiment can optionally be administered.

In a further aspect, the patient has or is at risk of developing a disorder that is treated with a beta blocker compound.

G protein-coupled receptors are the largest, most versatile and most ubiquitous of the several families of plasma membrane receptors. These receptors regulate virtually all known physiological processes in mammals. Moreover, they are the most common targets of currently used therapeutic drugs. Two classical examples of drugs that target these receptors are "β-blockers" and "angiotensin receptor blockers" (ARB's), which block or antagonize the β-adrenergic receptor for adrenaline or the receptor for angiotensin, respectively.

Drugs such as beta blockers that target G protein-coupled receptors have been developed based on a signaling paradigm in which stimulation of the receptor by an agonist (e.g., adrenaline) leads to activation of a "G protein", which then leads to second messenger stimulated signaling (e.g., via cAMP) and changes in physiological function (e.g., heart rate). "Blockers" competitively antagonize these actions. The stimulatory effects of agonists like adrenaline and angiotensin II on their respective receptors are also rapidly attenuated by a physiological process called "desensitization" (Koch et al, Annu Rev. Physiol. 62:237 (2000)). This occurs when stimulated receptors are modified by a G protein-coupled receptor kinase or other kinase which phosphorylates activated receptors and facilitates the binding to the phosphorylated receptor by a second molecule, β-arrestin, which then sterically interdicts further coupling to G proteins (Lefkowitz, J. Biol. Chem. 273: 18677 (1998)) and targets the receptor for internalization. This interaction between β-arrestin and the receptor shuts off further G protein signaling and leads to desensitization (Claing et al, Prog. Neurobiol. 66: 61 (2002)).

The inhibitors of EGLN3 and pVHL are administered, alone or in combination, with a therapeutically effective amount of a beta blocker. Examples of beta blockers that are used in accordance with the invention are acebutolol, atenolol, bisoprolol, metoprolol, nadolol, nebivolol, propranolol, and combinations thereof (See also, Goodman & Gilman's, *The Pharmacological Basis of Therapeutics*, McGraw-Hill Medical Publishing Division, Tenth Edition, pg. 249-260, 2001, incorporated herein by reference).

In another aspect, it is noted that G protein-coupled receptor kinase and β-arrestin mechanism not only desensitizes G protein signaling but also leads to signaling. There are compounds that act as agonists or antagonists of G protein-mediated signaling and as agonists of G-protein independent β-arrestin/G protein-coupled receptor kinase (GRK)-mediated signal transduction. While these compounds can act as "blockers", they can also stimulate cell protective pathways. In on other words, these β-arrestin/GRK compounds act as agonists or antagonists of G protein-mediated signaling and as agonists of β-arrestin/GRK-mediated signal transduction (see WO/2008/021552). The β-arrestin/GRK compounds are selected from the group consisting of carvedilol and alprenolol. Carvedilol is particularly effective in the treatment of heart failure.

In a preferred feature of this embodiment, the inhibitors are administered alone or in combination with beta blockers and/or NO donor compounds.

The inhibitors of EGLN3 and/or pVHL and the administration of these inhibitors are in accordance with this embodiment as discussed above. Additional active ingredients as discussed in this embodiment can optionally be administered.

In another aspect, the patient has or is at risk of developing hypertension.

The inhibitors of EGLN3 and pVHL are administered alone or in combination with a therapeutically effective amount of a beta blocker used to treat hypertension such as acebutolol, atenolol, bisoprolol, carvedilol, metoprolol, nadolol, nebivolol, propranolol (See also, Goodman & Gilman's, *The Pharmacological Basis of Therapeutics*, McGraw-Hill Medical Publishing Division, Tenth Edition, pg. 871-896, 2001, incorporated herein by reference).

In yet another aspect of this embodiment, the inhibitors are administered alone or in combination with the medications/drugs discussed above and/or NO donor compounds.

The inhibitors of EGLN3 and/or pVHL and the administration of these inhibitors are in accordance with this embodiment as discussed above. Additional active ingredients as discussed in this embodiment can optionally be administered.

In another aspect of this first embodiment, the patient has or is at risk of developing a disorder associated with nitric oxide donor desensitization of β2ARs. The inhibitors of EGLN3 and pVHL are administered alone or in combination with a therapeutically effective amount of a nitric oxide (NO) donor.

G-protein coupled receptors (GPCRs) include α-adrenergic receptors, β-adrenergic receptors, opioid receptors and prostaglandin receptors. Over time, when agonists are administered to activate the receptors, the receptors become desensitized, i.e., agonist administration no longer results in therapeutic activation of receptors and the receptors regardless of agonist administration are unable to control the pathologic condition, or may aggravate it.

When an agonist binds to a GPCRs to activate it, the receptor is phosphorylated. The phosphorylated receptor then moves to the interior of the cell it is associated with, i.e., internalized. The internalization often involves recruitment of β-arrestin. The receptor is recycled and moves to the surface of the cell where it is available to bind to an agonist.

The GPCRs have G-protein receptor kinases (GRKs) associated with them. The GRKs phosphorylate agonist-occupied receptors promoting binding of β-arrestin molecules. The β-arrestin molecules inhibit interactions between the receptors and G-proteins while also promoting internalization of the receptors. GRKs thus dampen signaling by the GPCRs. The typical result is a decreased level of GPCRs and desensitization.

NO donor compounds (e.g., S-nitrosoglutathione) inhibit the GRKs thereby allowing GPCRs to signal and to be recycled to the cell surface, i.e., thus preventing desensitization of the GPCRs and allowing GPCRs to be available in sufficient amount to control the disease event. NO donor compounds that are administered are those discussed above.

An NO donor compound as discussed above is administered.

The inhibitors of EGLN3 and/or pVHL and the administration of these inhibitors are in accordance with this embodiment as discussed above. Additional active ingredients as discussed in this embodiment can optionally be administered.

In another aspect, the patient can has or is at risk of developing an impaired secretion clearance of airways. When mucus secretion and mucus clearance are not in balance, excessive airway mucus can cause serious problems. This condition is called impaired airway clearance.

Excess, often sticky mucus may accumulate in the airways in conditions as varied as cystic fibrosis, cerebral palsy, and chronic obstructive pulmonary disease bronchiectasis. Retained secretions are a universal problem in people with artificial airways (tracheotomies) or those who depend on assisted ventilation. As a consequence of retained mucus, breathing becomes labored.

In yet another aspect of this embodiment, the inhibitors are administered alone or in combination with the medications/treatments as discussed above and/or a NO donor compound.

The inhibitors of EGLN3 and/or pVHL and the administration of these inhibitors are in accordance with this embodiment as discussed above. Additional active ingredients as discussed in this embodiment can optionally be administered.

In a further aspect, the patient can have or at be at risk of developing cystic fibrosis.

There are a number of treatments that are administered to ameliorate disorders associated with CF, such as lung, inflammation, digestive, hepatic, and biliary tract disorders. The inhibitors of the present invention are preferably administered in combination with these treatments.

Lung problems such as bacterial infections, inflammation and airway blockage can be treated with pharmaceutical and non-pharmaceutical methods.

To treat bacterial infections of the lung, doctors can prescribe a therapeutically effective amount of antibiotics such as aminoglycosides (e.g., tobramycin antipseudomonal penicillins, cephalosporins), and antimicrobial drugs (e.g., rifabutin, ethambutol, clarithromycin, clofazimine and aztreonam). Antibiotics are taken orally, by injection or inhaled (via an aerosol form).

For treating inflammation, doctors can prescribe a therapeutically effective amount of a nonsteroidal anti-inflammatory drugs or steroids, such as ibuprofen or prednisone. Additionally, pentoxifylline has been effective in decreasing inflammation.

For the treatment of airway blockage due to mucus buildup, a therapeutically effective amount of dornase alfa is prescribed.

In addition, CF patients are administered bronchial drainage or chest physiotherapy.

Digestive problems in CF patients are managed by eating a well-balanced, high-caloric diet that is low in fat and high in protein. Pancreatic enzyme and vitamin A, D, E and K supplements can also be administered.

The treatment of liver disease associated with CF can be oral dissolution therapy. Oral dissolution therapy comprises administering ursodeoxycholic acid in an amount sufficient to dissolve formations in the liver.

The treatment for gallbladder disease associated with CF is laparoscopic cholecystectomy. Laparoscopic cholecystectomy involves removing the gallbladder through a tiny incision in the navel.

In yet another aspect of this embodiment, the inhibitors are administered alone or in combination with the medications/drugs discussed above and/or NO donor compounds.

The inhibitors of EGLN3 and/or pVHL and the administration of these inhibitors are in accordance with this embodiment as discussed above. Additional active ingredients as discussed in this embodiment can optionally be administered.

In a further aspect, the patient can have or at be at risk of developing sickle cell disease.

Treatments for sickle cell anemia include administering a therapeutically effective amount of medications such as antibiotics, pain-relieving medications, hydroxyurea, butyric acid, clotrimazole, nitric oxide, and Flocor™ (Poloxamer 188). Patients of sickle cell anemia can also be treated with blood transfusions, supplemental oxygen, and bone marrow transplants.

In yet another aspect of this embodiment, the inhibitors are administered alone or in combination with the medications/drugs discussed above and/or NO donor compounds.

The inhibitors of EGLN3 and/or pVHL and the administration of these inhibitors are in accordance with this embodiment as discussed above. Additional active ingredients as discussed in this embodiment can optionally be administered.

The inhibitors and administration of inhibitors are in accordance with this embodiment as discussed above. Additional active ingredients as discussed in this embodiment can optionally be administered.

The patient can also have or at be at risk of developing an impaired sense of smell.

An impaired sense of smell is caused by a number of factors. Treatments include but are not limited to administering a therapeutically effective amount of decongestants, antihistamine-decongestants, histamine type 1 blockers, antibiotics, nasal steroids, zinc, copper, other trace metals, and allergy desensitization injections. Treatments can also include using nasal douches or correcting the impairment by surgery. Surgeries include septoplasty, rhinoplasty, and endoscopic sinus surgery.

In yet another aspect of this embodiment, the inhibitors are administered alone or in combination with the medications/drugs discussed above and/or NO donor compounds.

The inhibitors of EGLN3 and/or pVHL and the administration of these inhibitors are in accordance with this embodiment as discussed above. Additional active ingredients as discussed in this embodiment can optionally be administered.

ARDS is treated with mechanical ventilation in an Intensive Care Unit. Ventilation is usually delivered through orotracheal intubation, or tracheostomy.

Appropriate antibiotic therapy is also administered as soon as microbiological culture results are available.

The inhibitors of EGLN3 and pVHL are administered alone or in combination with these treatments.

In yet another aspect of this embodiment, the inhibitors are administered alone or in combination with the medications/drugs discussed above and/or NO donor compounds.

The inhibitors of EGLN3 and/or pVHL and the administration of these inhibitors are in accordance with this embodiment as discussed above. Additional active ingredients as discussed in this embodiment can optionally be administered.

We now turn to the second embodiment.

The second embodiment of the invention is a composition, comprising an inhibitor of EGLN3 or an inhibitor of pVHL, and an additional component.

The inhibitor of EGLN3 enzyme activity, alone or in combination, can also be combined with any pharmaceutically acceptable carrier or medium to form a composition.

The carriers or mediums are solvents, dispersants, coatings, absorption promoting agents, controlled release agents, and inert excipients. The inert excipients that are used in the composition include starches, polyols, granulating agents, microcrystalline cellulose, diluents, lubricants, binders, and disintegrating agents.

The composition is administered topically, enterally, parenterally by injection or infusion, or by other forms in a manner as discussed above for the inhibitors.

The composition is in the form of a tablet, cachet, pellet, gel, paste, syrup, bolus, electuary, slurry, capsule, powder, granules, a solution, suspension in an aqueous liquid, a non-aqueous liquid, an oil-in-water liquid emulsion, a water-in-oil liquid emulsion, or a liposomal formulation.

The orally administered composition can also include binders, lubricants, inert diluents, lubricating, surface active or dispersing agents, flavoring agents, and humectants. Orally administered formulations such as tablets are optionally coated or scored and are formulated to provide sustained, delayed or controlled release of the EGLN3 inhibitor.

In a further aspect, the composition is in a form for administration by intravenous injection, intramuscular injection, subcutaneous injection, intraperitoneal injection, topical injection, sublingual injection, intraarticular injection, intradermal injection, buccal administration, ophthalmic administration, or intranasaly.

The composition is in a form for transcutaneous administration such as a reservoir-type patch, matrix-type patch, or other form.

The composition can also be in a form so that the composition is administered by the pulmonary route, including but not limited to intratracheal instillation, intratracheal delivery of liposomes, insufflation and aerosol inhalation. Aerosols can also be used in intranasal applications.

In a further aspect, the composition also includes therapeutic ingredients, anti-caking agents, preservatives, sweetening agents, colorants, flavors, desiccants, plasticizers, dyes, or the like. The composition can contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, hydrates thereof, amino acids, alanine, glycine, betaine, peptides, proteins, and albumen.

The composition can also include an inhibitor of EGLN3 or pVHL and at least one additional active ingredient. The at least one additional active ingredient is in accordance with the active ingredients identified in the first embodiment.

In a further aspect, the combination of the inhibitor of pVHL or EGLN3 and additional active ingredient allows for the amount of inhibitor of pVHL or EGLN3 and/or additional active ingredients as discussed in the first embodiment to be present in the composition in amounts less than (e.g., 10-75%, 20-60%, 25-50%, or 30-40% less) those discussed in this application for the inhibitor and as conventionally prescribed for the active ingredients.

We now turn to the third embodiment.

The third embodiment of the invention is a kit. The kit contains an inhibitor of EGLN3 or pVHL in accordance with the first embodiment, a composition in accordance with the second embodiment, and optionally an additional active ingredient as discussed above.

The kit can also include instructions for practicing the method. In a further aspect, the kit contains a device used in connection with practicing the invention such as inhalers, syringes, cannulas, patches, microneedles, devices, etc. . . .

It is shown in the article by. Xie et al., "Oxygen-Regulated $\beta_2$—Adrenergic Receptor Hydroxylation by EGLN3 and Ubiquitylation by pVHL", Sci. Signal, 7 (July 2009), the whole of which is incorporated by reference, that EGLN3 serves as an O2-dependent $\beta$2AR prolyl hydroxylase. Following hydroxylation of the $\beta$2AR, the pVHL-E3 ligase complex, is recruited to and ubiquitylates the $\beta$2AR, promoting its down-regulation via proteosomal degradation). The present invention is further explained and exemplified by the following background examples and working examples as follows:

EXAMPLE I

A 60-year-old white male with asthma, wherein symptoms are not improving despite receiving treatment with 250 ug beclomethasone taken in combination with an inhaler containing albuterol (when needed) is begun on DMOG at a dose of 20 mg/kg three times per day. Patient's asthma improves.

EXAMPLE II

A 55-year-old white male with asthma exacerbated by treatment with budesonide and formoterol at a dose per actuation of 160 and 4.5 mcg, respectively. Patient is begun on DMOG at a dose of 100 mg/kg once per day. Patient's asthma improves.

EXAMPLE III

A 57-year-old white female with asthma exacerbated by treatment with fluticasone and salmeterol. Patient is begun on DMOG at a dose of 30 mg/kg twice per day. Patient's asthma improves.

EXAMPLE IV

A 60-year-old white female with asthma exacerbated wherein symptoms are not improving despite receiving treatment with albuterol. Patient is begun on DMOG at a dose of 25 mg/kg three times per day. Patient's asthma improves.

EXAMPLE V

A 55-year-old white male presents with severe coronary disease, heart failure, and an ejection fraction of 25% is started on carvedilol without ejection fraction improving. The patient is started on nitroglycerin patch (Nitro-bid), 2 inches, twice a day and DMOG at a dose of 100 mg/kg once per day. Ejection fraction improves to 40% within one month.

EXAMPLE VI

A 45-year-old white male presents with severe coronary disease, heart failure, and an ejection fraction of 25% is started on carvedilol at 50 mg BID without ejection fraction improving. The patient is started on nitroglycerin patch (Nitro-bid), 2 inches, twice a day and DMOG at a dose of 25 mg/kg three times per day. Ejection fraction improves to 42% within one month.

EXAMPLE VII

A 55-year-old Hispanic male presents with severe coronary disease, heart failure, and an ejection fraction of 25% is started on carvedilol at 25 mg divided BID without ejection fraction improving. The patient is started on intravenous nitroglycerin at 20 μg per minute and DMOG at a dose of 50 mg/kg three times per day. Ejection fraction improves to 42% within one month.

EXAMPLE VIII

A 63-year-old white male with lymphoma and muscle wasting. Patient is started on carvedilol at 12.5 BID and isosorbide dinitrate at 10 mg POTID. Patient is started on an intravenous formulation of DMOG at a concentration of 25.0 mg/m. Patient's strength improves as evidenced by a six minute walk test.

EXAMPLE IX

A 54-year-old white male with lymphoma and muscle wasting. Patient is started on alprenolol and isosorbide dinitrate. Patient is started on an intravenous formulation of DMOG at a concentration of 20.0 mg/mL. Patient's strength improves as evidenced by a six minute walk test.

EXAMPLE X

A 45 year old Hispanic female with hypertension and not responding to hydralazine hydrochloride (i.e., blood pressure 180/95). Patient is started on beta blocker (i.e., propranolol) without improvement. Patient is begun on DMOG at a dose of 30 mg/kg twice per day. Patient improves (i.e., blood pressure 160/90).

EXAMPLE XI

A 27-year-old white female with hypertension is given 2 inches of nitropaste with no improvement in symptoms. She is started on DMOG at a dose of 30 mg/kg twice per day. Patient improves. No limiting hypertension is noted.

EXAMPLE XII

A 56-year-old with unstable angina on IV nitroglycerin develops tolerance over 48 hours as evidenced by recurrent chest pains despite increasing doses of drug. Patient is started on an intravenous formulation of DMOG at a concentration of 15.0 mg/mL Patient responds to nitroglycerin.

EXAMPLE XIII

A 55 year old African American male with hypertension is not responding to hydralazine hydrochloride (i.e., blood pressure 180/95). Patient is started on beta blocker (i.e., metoprolol) without improvement. Patient is begun on DMOG at a dose of 30 mg/kg twice per day. Patient improves (i.e., blood pressure 160/90).

EXAMPLE XIV

A 56-year-old male with unstable angina on IV nitroglycerin develops tolerance over 48 hours as evidenced by recurrent chest pains despite increasing doses of drug. He is given an intravenous formulation of DMOG at a concentration of 10.0 mg/ml. The patient improves.

EXAMPLE XV

A 42-year old patient has Chronic Obstructive Pulmonary Disease and is treated with albuterol with no improvement. Patient started on DMOG at a dose of 50 mg/kg three times per day. Patient improves as evidenced by improved spirometry.

EXAMPLE XVI

A 56-year old patient having Chronic Obstructive Pulmonary Disease, receiving supplemental oxygen and treated with salbutamol and prednisone is started on DMOG at a dose of 20 mg/kg three times per day. Patient no longer requires supplemental oxygen.

EXAMPLE XVII

A 57-year-old white male with heart failure remains short of breath despite increasing doses of nitroglycerin. The patient is begun on 0.1 µg/kg/min of S-nitrosoglutathione with improvement of dyspnea and relief of angina.

EXAMPLE XVIII

A 15-year-old white female with cystic fibrosis presents with hypoxemia and pulmonary hemorrhage. She is begun on ethyl nitrite 20 parts per million in nitrogen, N-acetylcysteine 50 mg/kg Q 6 hours and ascorbate IV 1 gram Q 6 hours, along with DMOG at a dose of 40 mg/kg three times per day. Over the following three days the hemorrhage stops and the patient reverts to normal state of health. She is discharged on day 7.

EXAMPLE XIX

A 17-year-old female with cystic fibrosis presents with labored breathing and increased sputum production. She is begun on HNO 10 ppm in nitrogen with improvements in her symptomatic status. She is begun on a dose of DMOG at 20 mg/kg three times per day with decreases in sputum production over two days.

EXAMPLE XX

A 16-year old black female with homozygous sickle cell disease presents in crisis. The patient complains of severe abdominal and chest pain and is somewhat disoriented. She receives two units of blood while being administered 80 ppm inhaled ethyl nitrite and 100 mg/kg of DMOG. All symptoms resolve.

EXAMPLE XXI

A 30-year-old white male presents complaining of shortness of breath. A chest X-ray reveals pulmonary edema. An intravenous line is inserted and the patient is started on IV infusion of 0.1 mg per kilogram per minute nitroglycerin. He is also given an intravenous formulation of DMOG at a concentration of 10.0 mg/ml. His symptoms improve over the day, during which time his arteriolar $PO_2$ increases from 70 to 85 mm Hg.

EXAMPLE XXII

A 40-year-old white male presents complaining of shortness of breath. A chest X-ray reveals pulmonary edema. The patient is started on intravenous nitroglycerin at 25 µg per minute and DMOG at a dose of 25 mg/kg three times per day. His symptoms improve over the day, during which time his arteriolar $PO_2$ increases from 60 to 85 mm Hg.

EXAMPLE XXIII

A 42 year old patient having an impaired sense of smell is treated with a steroidal nasal spray with no improvement. DMOG is administered via nasal spray in amount 1 mg/ml. Patient sense of smell improves.

EXAMPLE XXIV

A 55-year-old Caucasian male with asthma exacerbated by treatment with budesonide and formoterol at a dose per actuation of 150.0 and 5.0 mcg, respectively. Patient is begun on malonic acid compound at a dose of 120 mg/kg once per day. Patient's asthma improves.

EXAMPLES XXV-XLIX

EXAMPLES I-XXIV are repeated with the exception that a medication containing a sufficient amount of SiRNA (e.g., sense, 5'-GCAAAUACUACGUCAAGGAUU-3' (SEQ ID NO: 1); antisense, 5'-UCCUUGACGUAGUAUUUGCUU-3' (SEQ ID NO: 2) and sense, 5'-UUCAGGAAUUUAACUAG-GAUU-3' (SEQ ID NO: 3); and antisense, 5'-UCCUAG-UUAAAUUCCUGAAUU-3' (SEQ ID NO: 4); Genbank Accession Number, EGLN3 NM_022703) as the inhibitor in amount of 1-250 mg administered once-daily, twice-daily or three times-daily, continuously (every day) or intermittently. The patient exhibits improvement in each EXAMPLE.

EXAMPLES XLIX-LXXII

EXAMPLE I-XXIV are repeated with the exception that a medication containing the peptide comprising the amino acid sequence of EAISFLLSLIDRLVLY is administered as the inhibitor in amount of 10-100 mg administered orally once-daily, twice-daily or three times-daily, continuously (every day) or intermittently. The patient exhibits improvement in each EXAMPLE.

Variations

The foregoing description of the invention has been presented describing certain operable and preferred aspects. It is not intended that the invention should be so limited since variations and modifications thereof will be obvious to those skilled in the art, all of which are within the spirit and scope of the invention.

What is claimed is:
1. A method for treating asthma, comprising:
    administering to a patient in need thereof a therapeutically effective amount of an inhibitor of EGLN3,
    wherein the inhibitor of EGLN3 is DMOG.

2. The method according to claim 1, further comprising administering to the patient a therapeutically effective amount of a beta agonist for treating asthma.

3. The method according to claim 2, wherein the beta agonist for treating asthma is selected from the group consisting of salmeterol, formoterol, bambuterol, albuterol, salbutamol, levalbuterol, terbutaline, bitolterol, and mixtures thereof.

\* \* \* \* \*